(12) United States Patent
Schiffler et al.

(10) Patent No.: US 8,982,343 B2
(45) Date of Patent: Mar. 17, 2015

(54) OPTICAL ANALYZER HAVING A HOLDER FOR INSTALLATION IN A GAS-CARRYING HOLLOW SPACE

(75) Inventors: Ingo Schiffler, Freiburg (DE); Sebastian Matt, Mühlenbach (DE)

(73) Assignee: Sick AG, Waldkirch (DE)

( * ) Notice: Subject to any disclaimer, the term of this patent is extended or adjusted under 35 U.S.C. 154(b) by 173 days.

(21) Appl. No.: 13/326,450

(22) Filed: Dec. 15, 2011

(65) Prior Publication Data

US 2012/0154799 A1    Jun. 21, 2012

(30) Foreign Application Priority Data

Dec. 21, 2010 (EP) ..................................... 10196301

(51) Int. Cl.
*G01N 1/10* (2006.01)
*G01N 21/03* (2006.01)
*G02B 7/00* (2006.01)

(52) U.S. Cl.
CPC ............ *G01N 21/0317* (2013.01); *G02B 7/007* (2013.01)
USPC ........................................................ 356/246

(58) Field of Classification Search
CPC ........................... G02B 7/007; G01N 21/0317
USPC ........................................................ 356/246
See application file for complete search history.

(56) References Cited

U.S. PATENT DOCUMENTS

| | | | | |
|---|---|---|---|---|
| 3,897,139 A | * | 7/1975 | Caruolo et al. | ............... 359/873 |
| 4,515,336 A | * | 5/1985 | Fischer | .................... 248/288.51 |
| 4,622,465 A | | 11/1986 | Harig et al. | |
| 5,596,404 A | * | 1/1997 | Beck et al. | ..................... 356/301 |
| 7,145,145 B2 | * | 12/2006 | Benson | .................... 250/339.07 |
| 2004/0232340 A1 | | 11/2004 | Benson | |

OTHER PUBLICATIONS

European Search Report cited in corresponding German Patent Application No. 10196301.5, dated Apr. 27, 2011, six (6) pages.

* cited by examiner

*Primary Examiner* — Michael A Lyons
*Assistant Examiner* — Shawn Decenzo
(74) *Attorney, Agent, or Firm* — Nath Goldberg & Meyer; Jerald L. Meyer; Katelyn J. Bernier

(57) ABSTRACT

An optical analyzer, in particular an optical gas analyzer, having a holder (10) for installing into a gas-carrying hollow space, wherein the holder (10) has a ball socket (20) and a ball segment (30) with a longitudinal axis (A), wherein the ball socket (20) has at least one first segment (21) and a second segment (22) and is designed such that it at least partly engages around the ball segment (30) in the direction of the longitudinal axis (A).

7 Claims, 1 Drawing Sheet

OPTICAL ANALYZER HAVING A HOLDER FOR INSTALLATION IN A GAS-CARRYING HOLLOW SPACE

The invention relates to an optical analyzer having a holder for installation into a gas-carrying hollow space.

BACKGROUND OF THE INVENTION

Optical analyzers, in particular optical gas analyzers which are installed in gas-carrying hollow spaces, are known. The gas analyzers are in this respect inserted into an opening in the wall of the gas-carrying hollow space. Since pressures of up to 20 bar are often present in the gas-carrying hollow spaces, it is necessary that the holders are designed for corresponding pressures. It is furthermore necessary that the gas analyzers have a holder via which the inclination of the gas analyzers can be set in two axes relative to the gas-carrying hollow space since the holders can often not be inserted, in particular welded, into the opening of the gas-carrying hollow space with the required precision. Holders are known which are sealed with the aid of a rubber band which is spanned over two flange surfaces tiltable relative to one another. It is alternatively likewise known to place an O ring of rubber between two flanges and to tighten the flange screws accordingly until the desired inclination angle is reached. Such seals, however, do not withstand high pressure differences.

Furthermore, holders are known with two flanges between which a metal bellows is inserted, with the inclination of the two flanges relative to one another being able to be varied with the aid of threaded bars, bolt nuts and locknuts. Such a holder, however, has the consequence of a long construction shape. In addition, dust or other contamination can collect in the interior in the undercuts of the bellows. A cleaning of the bellows is furthermore extremely difficult and/or expensive.

Finally, holders are known in which a ball segment is inserted in a single-part ball socket. There is, however, the danger at high pressures that the ball segment is pressed out of the ball socket. Apparatus are also known in which a pressure-tight window in front of the adjustment apparatus prevents high pressure or contamination from the gas-carrying measurement space from acting on the adjustment device. Such a window is, however, disadvantageously associated with high costs and installation effort. It can become dirty very easily and has a negative effect on the optics.

A holder is known from US 2004/0232340 A1 in which the analyzer is fixedly connected to a gas-carrying line. A spherical window holder is provided in the holder in order to be able to unscrew the window from the actual beam path for cleaning and to be able to clean it in a cleaning chamber.

A holder is known from U.S. Pat. No. 4,622,465 for a quartz double window which serves for coupling measurement light into a liquid-carrying hollow space. In this respect, one window is in contact with the inner space and the other window is in contact with the outer space. The respective outwardly disposed window can be cleaned. To be able also to clean the inwardly disposed window, the quartz double window is seated in a spherical holder which is supported in a ball socket comprising two ball segments so that the quartz double window can be rotated about 180° and the inner window and outer window then swap their positions.

It is therefore the object of the invention to provide an optical analyzer having a holder for installation into a gas-carrying hollow space, with the holder also withstanding pressures of up to 20 bar, and with it, however, being of a simpler structure overall and being in particular easy to operate and simple to clean.

The object is satisfied in accordance with the invention by an optical analyzer having a holder for installation into a gas-carrying hollow space having the feature of claim 1.

Advantageous aspects and further developments of the invention are set forth in the dependent claims.

DETAILED DESCRIPTION OF THE INVENTION

The optical analyzer in accordance with the invention, which is in particular an optical gas analyzer, having a holder for installation of the analyzer into a gas-carrying hollow space, with the holder having a ball socket and a ball segment with a longitudinal axis, is characterized in that the ball socket has at least one first segment and one second segment and is designed such that it engages around the ball segment at least partly in the direction of the longitudinal axis. A partial engaging around is to be understood such that the inner surface of the ball socket has contact at both sides of a largest diameter of the ball segment in sections perpendicular to the longitudinal axis of the ball segment. The ball segment is thus fixed on a partial engaging around by the ball socket in the direction of the longitudinal axis. Forces in both directions can thus in particular be taken up along the longitudinal axis. A pressing of the ball segment out of the ball socket is thus no longer possible. The holder is thus in particular suitable for pressures of up to 20 bar. A sufficient seal tightness even at high pressures is ensured by introduction of one or more seals between the ball socket 20 and the ball segment 30.

The inclination of the ball socket relative to the ball segment and thus the inclination, that is adjustment, of the analyzer relative to the hollow space is fixable by means of at least two threaded bars, preferably by means of four threaded bars, which allows a simple construction of the holder.

The threaded bars are preferably connected to the ball socket at one end and are directly or indirectly fixable to the ball segment with the aid of bolt nuts at their other end. It is naturally likewise possible to arrange the threaded bars at one end at the ball segment and to fix their other end to the ball socket with the aid of bolt nuts.

In a variant, two bolt nuts are provided at each threaded bar, namely a bolt nut and a locknut, with the aid of which the inclination between the ball socket and the ball segment can be set. It is, however, disadvantageous in this respect that no stepless setting of the inclination is possible. In accordance with a particularly preferred embodiment of the invention, a spring element is therefore arranged between the ball socket and the ball segment. It is thus possible in each case only to provide one bolt nut per threaded bar and to tighten it against the spring force to be able to set the inclination steplessly between the ball socket and the ball segment.

In accordance with a particularly preferred embodiment of the invention, a helical spring or a plate spring is arranged between the ball socket and the ball segment about at least one of the threaded bars, whereby a stepless adjustment of the inclination between the ball socket and the ball segment is made possible in a particularly simple and inexpensive manner.

BRIEF DESCRIPTION OF THE DRAWINGS

An embodiment of the invention will be explained in detail with reference to the following Figures. There are shown.

DETAILED DESCRIPTION OF THE DRAWINGS

Figure 1:
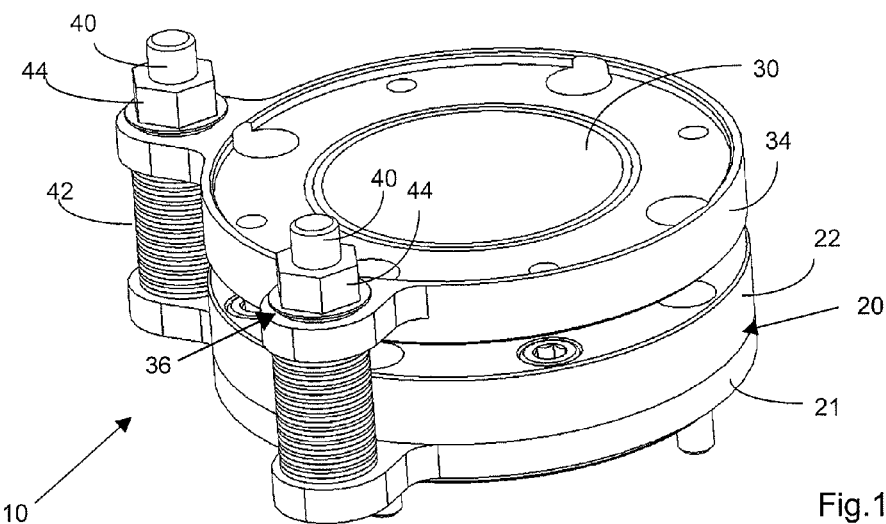
FIG. 1 a perspective view of the embodiment of a holder in accordance with the invention.
Figure 2:
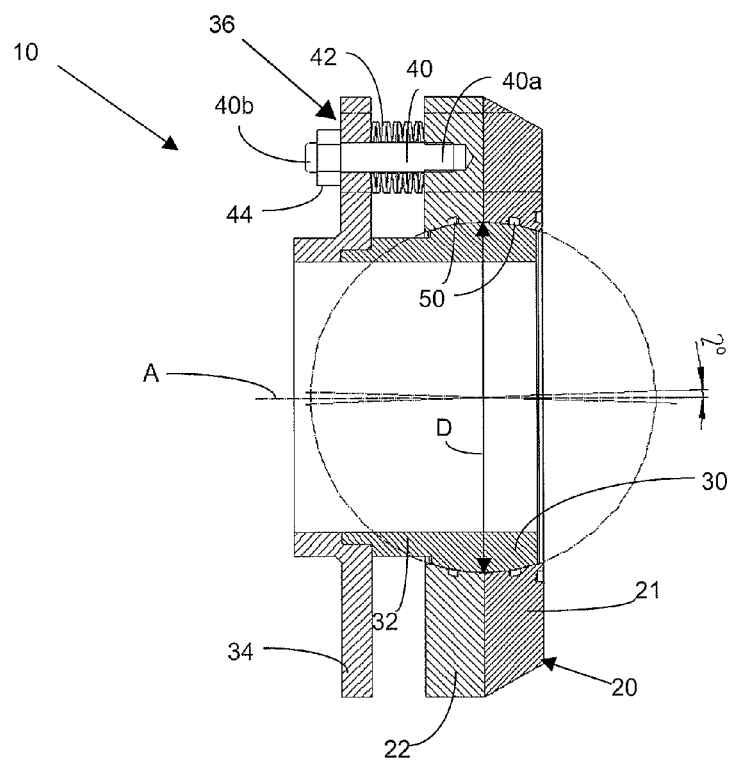
FIG. 2 a longitudinal section through the holder in accordance with FIG. 1.

FIGS. 1 and 2 show a perspective view and a longitudinal section of a holder 10 for the installation of optical analyzers, in particular optical gas analyzers, into a gas-carrying hollow space. The holder 10 has a ball socket 20 and a ball segment 30 supported in the ball socket. The ball segment 30 can in this respect be fixedly connected to the optical analyzer, whereas the ball socket 20 is fixedly connected to the wall of the gas-carrying hollow space. The inclination of the gas sensor can thus be varied, in particular in two axes, relative to the gas-carrying hollow space by tilting the ball segment 30 in the ball socket 20.

The ball socket 20 is designed such that it at least partly engages around the ball segment 30 in the direction of the longitudinal axis A of the ball segment 30. Viewed along the longitudinal axis A of the ball segment 30, the ball socket 20 contacts the ball segment 30 at both sides of a largest diameter D of sections perpendicular to the longitudinal axis A of the ball segment 30 for this purpose. The ball socket 20 thus fixes the ball segment 30 in the direction of the longitudinal axis A.

To be able to introduce the ball segment 30 into the ball socket 20, the ball socket 20 has a first segment 21 and a second segment 22 between which the ball segment 30 is inserted. The ball segment 30 can be tilted in the ball socket 20, but cannot be pressed out of the ball socket 20 after the joining of the two segments 21, 22 of the ball socket 20.

A cylindrical section 32 is shaped at the ball segment 30 and its longitudinal axis coincides with the longitudinal axis A of the ball segment 30. A fastening ring 34 is arranged at the free end of the cylindrical section 32 facing the ball segment 30.

The inclination of the ball segment 30 relative to the ball socket 20 is fixed by means of two threaded bars 40 which are arranged at the fastening ring 34 of the ball segment 30 and at the second segment 22 of the ball socket 20. The threaded bars 40 in this respect have a first end 40a and a second end 40b, with the first end 40a of the threaded bar 40 each being fixedly and non-rotatably connected to the second segment 22 of the ball socket 20. The second end 40b of the threaded bar 40 is guided through a passage opening 36 of the fastening ring 34. The relative position of the fastening ring 34 with respect to the threaded bar 40 can be fixed by means of two nuts screwed onto the threaded bar 40 at both sides of the fastening ring 34. In the present embodiment, however, a helical spring 42 is provided between the second segment 22 of the ball socket 20 and the fastening ring 34, whereas a respective bolt nut 44 is only screwed onto the threaded bar 40 on the side of the fastening ring 34 remote from the ball socket 20. The bolt nut 44 can be tightened on the threaded bar 40 against the spring force of the helical spring 42 to vary and fix the relative position of the fastening ring 34 with respect to the threaded bar 40 and thus the inclination of the ball segment 30 with respect to the ball socket 20. An inclination of the ball segment 30 with respect to the ball socket 20 is in particular possible by ±2° about the longitudinal axis A. In this respect, a stepless change of the inclination is in particular possible by use of the bolt nut 42.

A short construction shape of the holder 10 is made possible by the use of the ball segment in the ball socket, said holder withstanding even high pressures of up to 20 bar due to the fixing along the ball segment 30 along the longitudinal axis A in both directions and additionally being easy to operate and simple to clean. By introducing one or more seals 50 into the inner surface of the ball socket 20 between the ball socket 20 and the ball segment 30, sufficient seal tightness can also be ensured for toxic gases even at high pressures.

REFERENCE NUMERAL LIST 10 holder
20 ball socket
21 first segment
22 second segment
30 ball segment
32 cylindrical section
34 fastening ring
36 passage opening
40 threaded bar
40a first end
40b second end
42 helical spring
44 bolt nut
50 seal
A longitudinal axis
D diameter

The invention claimed is:

1. An optical analyzer comprising:
a holder (10) for installing the analyzer into a gas-carrying hollow space and withstanding pressures up to 20 bar, the holder (10) comprising:
a ball socket (20), having a first segment (21) and a second segment (22) and an inner surface; and
a ball segment (30) having a longitudinal axis (A) and a fastening ring (34),
wherein the ball segment (30) is inserted between the first and second segments (21, 22), the inner surface directly contacting both sides of a largest diameter (D) of the ball segment (30) perpendicular to the longitudinal axis (A) to thereby fix the ball segment (30) along the longitudinal axis (A) in both directions when the first and second segments (21, 22) are joined, and an inclination of the ball segment (30) relative to the ball socket (20) about the longitudinal axis (A) is fixed by means of at least two threaded bars (40), which are each positioned through a respective passage opening (36) in the fastening ring (34);
wherein the ball segment (30) is fixedly connected to the optical analyzer;
wherein the ball socket (20) is fixedly connected to a wall of the gas-carrying hollow space; and
wherein at least one seal (50) is provided between the ball socket (20) and the ball segment (30).

2. An optical analyzer in accordance with claim 1, wherein the threaded bars (40) are fixedly connected to the ball socket (20) at one end (40a) and are directly or indirectly fixable to the ball segment (30) at the other end of the threaded bars (40b) with the aid of bolt nuts (44).

3. An optical analyzer in accordance with claim 1, wherein a spring element (12) is arranged between the ball socket (20) and the ball segment (30).

4. An optical analyzer in accordance with claim 2, wherein a helical spring (42) or a plate spring is arranged around at least one of the threaded bars (40) between the ball socket (20) and the ball segment (30).

5. An optical analyzer in accordance with claim 3, wherein a helical spring (42) or a plate spring is arranged around at least one of the threaded bars (40) between the ball socket (20) and the ball segment (30).

6. An optical analyzer in accordance with claim 1, wherein the inclination is adjustable within two degrees about the longitudinal axis (A).

7. An optical analyzer comprising:
a holder (10) for installing the analyzer into a gas-carrying hollow space and withstanding pressures up to 20 bar, the holder (10) comprising:
- a ball socket (20), having a first segment (21) and a second segment (22) and an inner surface;
- a ball segment (30) having a longitudinal axis (A) and a fastening ring (34); and
- a cylindrical section molded at the ball segment, extending from the second segment (22) along the longitudinal axis (A) to a free end, the free end attached to the fastening ring (34) of the ball segment (30) such that the fastening ring (34) faces the ball segment (30), wherein the ball segment (30) is inserted between the first and second segments (21, 22), the inner surface directly contacting both sides of a largest diameter (D) of the ball segment (30) perpendicular to the longitudinal axis (A) to thereby fix the ball segment (30) along the longitudinal axis (A) in both directions when the first and second segments (21, 22) are joined, and an inclination of the ball segment (30) relative to the ball socket (20) about the longitudinal axis (A) is fixed by means of at least two threaded bars (40) which are each positioned through a respective passage opening (36) in the fastening ring (34);

wherein the ball segment (30) is fixedly connected to the optical analyzer;

wherein the ball socket (20) is fixedly connected to a wall of the gas-carrying hollow space; and wherein at least one seal (50) is provided between the ball socket (20) and the ball segment (30).

* * * * *